Figure 1:
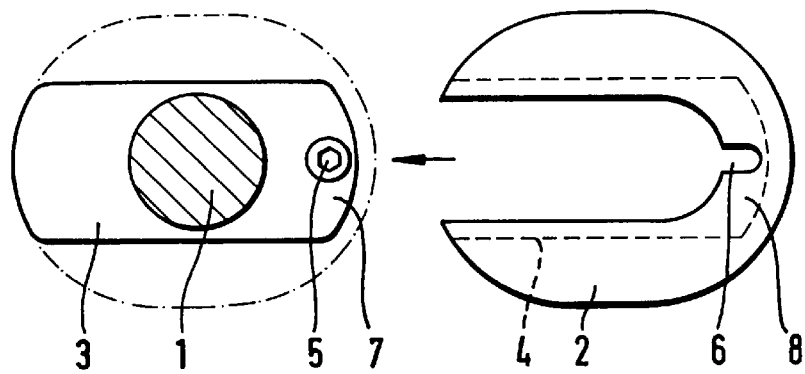

United States Patent [19]
Keller

[11] Patent Number: 5,976,189
[45] Date of Patent: Nov. 2, 1999

[54] ASSEMBLY COMPRISING A JOINT ENDOPROSTHESIS

[75] Inventor: Arnold Keller, Kayhude, Germany

[73] Assignee: Waldemar Link (GmbH & Co), Germany

[21] Appl. No.: 09/047,287

[22] Filed: Mar. 24, 1998

[30] Foreign Application Priority Data

Mar. 26, 1997 [DE] Germany ............ 297 05 499 U

[51] Int. Cl.⁶ .................................................. A61F 2/30
[52] U.S. Cl. ................................................................ 623/18
[58] Field of Search .................................. 623/20, 21, 23, 623/18

[56] References Cited

U.S. PATENT DOCUMENTS 3,806,957   4/1974   Shersher ........................... 623/23

FOREIGN PATENT DOCUMENTS

| 0 158 014 | 10/1985 | European Pat. Off. . | |
|---|---|---|---|
| 0 385 930 A1 | 9/1990 | European Pat. Off. | 623/23 |
| 0 649 639 | 4/1995 | European Pat. Off. . | |
| 0 654 255 | 5/1995 | European Pat. Off. . | |
| 2 602 672 | 2/1988 | France . | |
| 640 132 | 12/1983 | Switzerland . | |

OTHER PUBLICATIONS

Link® Ribbed System, Cementless Total Hip Joint Prostheses, Modular System, Rippensystem 'Rib System', Waldemar Link (GmbH & Co.), pages: cover, information page, 1–11, and 22–25.

*Primary Examiner*—David H. Willse
*Attorney, Agent, or Firm*—Medlen & Carroll, LLP

[57] ABSTRACT

Joint endoprosthesis with an attachment part which can be attached and removed along a guide provided on the endoprosthesis, and with a screw (5) for locking the attachment part. This screw is arranged in the area of overlapping surface portions (7, 8) of the prosthesis and of the attachment part. A first surface portion (7) includes a threaded bore (13) receiving the screw (5). The screw shank has, adjacent to the screw head (10), a threaded section (12), adjacent to this a section (14) of reduced thickness, and adjacent to this a thickened end (15). The section (14) of reduced thickness lies in the area of the second surface portion (8), and namely in a slit (6) which extends in the direction of the guide and whose width is smaller than the thickness of the thickened end (15).

18 Claims, 1 Drawing Sheet

ASSEMBLY COMPRISING A JOINT ENDOPROSTHESIS

Endoprosthesis attachment parts which are attached during implantation, or removed in a follow-up operation, should be fastened and secured in the simplest possible way, so that this procedure demands as little attention and manual dexterity as possible. To connect an endoprosthesis to an attachment part, it is known to provide cooperating guide means on the prosthesis and the attachment part, which guide means can be easily pushed one into the other and take on a considerable part of the force transmission during the use of the prosthesis. The securing of the attachment part can in this case be limited to preventing its relative movement along the guide. It is known to use a screw for this purpose, which screw is provided in the area of overlapping surface portions of the prosthesis and of the attachment part. One of these surface portions includes a threaded bore which receives the screw. The other surface portion includes a recess which receives a part of the screw when the latter is in its securing end position. One example of this is a known hip-joint endoprosthesis (brochure from Waldemar Link (GmbH & Co): "Rippensystem" [Rib System]) whose stem, to be inserted into the femur, ends in a neck bearing which can be attached and removed for the most part along a slide guide provided on the stem. An attachment provided on the stem, and extending parallel to the neck bearing, includes a bore through which a screw is introduced into a threaded bore provided in the neck bearing. This demands skill.

The invention is therefore based on the object of making available a joint endoprosthesis which is of the type specified as part of an assembly, and in which the securing of the attachment part demands less attention and skill. The solution lies in the features of a first surface portion comprising a threaded bore configured to receive a screw; a screw positioned in the first surface position, said screw comprising a top section, adjacent first and second middle sections, and a bottom section, said top section comprising a head, said first middle section comprising a thread configured to fit in said threaded bore, said second middle section comprising a section of reduced thickness having a length, and said bottom section comprising an end having a thickness greater than that of said section of reduced thickness; and a removable attachment comprising a second surface portion having a thickness, said second portion comprising a slit having a width, said slit surrounding said section of reduced thickness of said screw. Preferably the features include embodiments wherein the width of the slit is smaller than the thickness of the end of the screw; the slit comprises an open end and a closed end; the closed end of the slit comprises a recess which at least partially receives the end of the screw; the end of the screw has a cone surface directed towards the slit; the length of the section of reduced thickness is at least as great as the thickness of the second surface portion; the screw head comprises a structure configured for receiving a screwdriver; and the end of the screw comprises a structure configured for receiving a screwdriver.

Before applying the attachment piece, care is taken to ensure that the screw is screwed into the threaded bore of the first surface portion as far as its end position. It is thus situated in the ready-to-secure position and does; not need to be held loosely in a defined position. Nor does its axial positioning need to be attended to during the operation, because it can be turned as far as the limit stop in preparation. An error is not possible here. The section of reduced thickness, which adjoins the threaded section, then lies in the area in which the second surface portion of the attachment part is expected. The latter has, at the appropriate location, a slit which is arranged in such a way that it receives the section of reduced thickness when the attachment part is pushed into the guide. The thickened end of the screw then lies, as viewed from the first surface portion, on the other side of the second surface portion and at a certain distance therefrom which permits the displacement of the attachment part. Once the attachment part has reached its desired end position, the screw is turned back until the thickened end of the screw engages on the second surface portion, namely on the edges of the slit, and thereby fixes the attachment part. The operating surgeon therefore needs simply to turn the screw from its one end position to the other one. This does not demand any particular attention. Only a short turning of the screw is needed because only the distance from the one end position to the other needs to be negotiated, which distance can be very small and can be negotiated with a fraction of a full rotation of the screw. Repeated gripping of the screwdriver is generally not required.

The cooperation of the thickened screw end with the edges of the slit provided in the second surface portion does not generally demand any positive locking for the securing function. The pressing which is obtained on tightening the screw into its end position is sufficient. However, positive locking can be provided if so desired, for example by providing the closed end of the slit with a recess which at least partially receives the thickening. In addition to or instead of this, the side of the thickened screw end facing the slit can be designed in a conical shape and can thus lead to plastic deformation even upon slight tightening of the screw, which plastic deformation not only secures the attachment part, but also results in such great friction on the screw that the latter cannot come loose from its end position by chance The threaded bore is preferably provided in that surface portion which is more easily accessible, in which case the screw head, which for example has a hexagon for cooperating with the screwdriver, is facing towards the operating surgeon. However, the reverse arrangement is also conceivable. Then the thickened end of the screw should be provided with an attachment structure, for example a hexagon, for the turning instrument.

Figure 2:
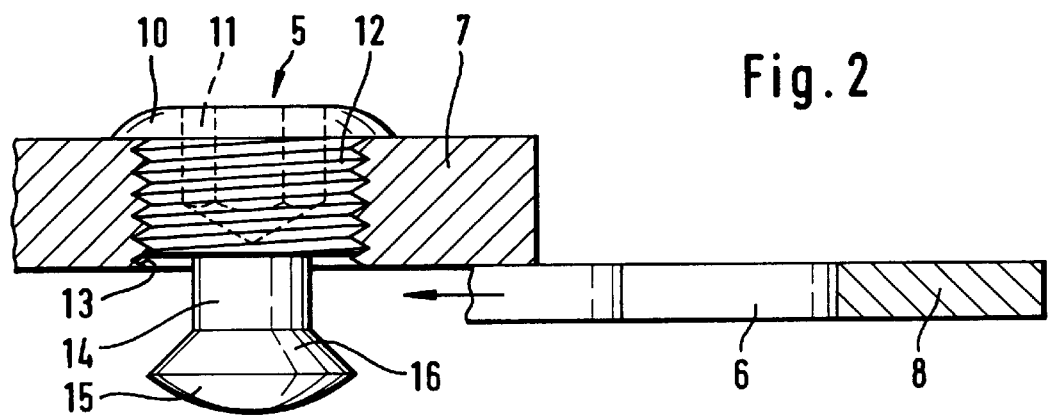
Figure 3:
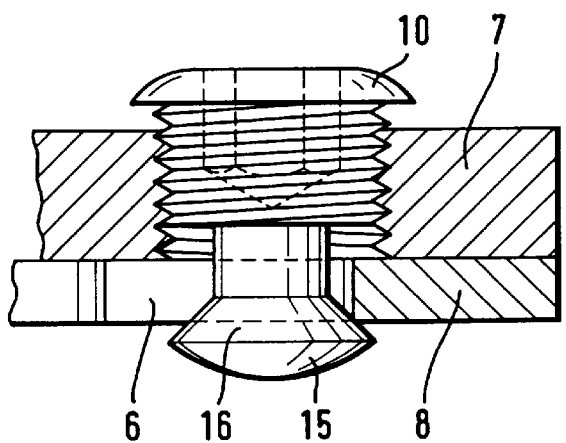

The invention is explained in greater detail below, with reference to the drawing which depicts an advantageous illustrative embodiment and in which:

FIG. 1 shows the plan view of the upper area of a femoral hip prosthesis, with a neck bearing which is to be pushed on, FIG. 2 shows the screw area of the same femoral hip prosthesis, in an enlarged cross-sectional representation prior to securing, and FIG. 3 shows the state after securing.

The hip prosthesis, whose neck 1 can be seen in section, has a removable neck bearing 2 which is to be pushed onto a collar part 3 of the prosthesis. For this purpose, use is made of guide arrangements which are known per se and which are therefore not represented in detail, their contour being indicated by a broken line at 4. The position of the neck bearing after it has been pushed on is indicated on the left by a dot-and-dash line. For securing the neck bearing in the pushed-on position, a screw 5 is used whose shank is received by a slit 6 in the neck bearing. The screw 5 sits in a surface portion 7 of the collar 3. The associated slit 6 is arranged in a surface portion 8 of the neck bearing.

These surface portions can be seen in FIG. 2 in the state before the pushing-on of the neck bearing has been completed. The slit 6 has not yet reached the screw 5.

The screw 5 consists of a head 10 with internal hexagon 11 for the engagement of a screwdriver, a thread 12 which sits in a threaded bore 13 of the surface portion 7 and whose axial length is not greater than the thickness of the surface portion 7, a section of reduced thickness 14, and a thickened end 15 which directs a conical surface 16 towards the threaded section. In the ready-to-secure state, the screw is completely screwed into the surface portion 7 so that the head lies on its top surface. In this state, the free length of the section 14 of reduced thickness is at least as great as the thickness of the surface portion 8.

After the surface portion 8 has reached its end position, in which its slit 6 surrounds the section 14 of reduced thickness, the screw 5 is turned so that its head 10 moves off the face of the surface portion 7. In so doing, the thickened end 15 of the screw approaches the surface portion 8, until finally its cone surface 16 grips the edges of the slit 6. When the screw has been sufficiently turned to the position which is shown in FIG. 3, it secures the surface portion 8 or neck bearing 2 in its functional position.

I claim:

1. An assembly, comprising:
   a) a joint endoprosthesis comprising a first surface portion, said first surface portion comprising a threaded bore configured for receiving a screw;
   b) a screw positioned in said first surface portion, said screw comprising a top section, adjacent first and second middle sections, and a bottom section, said top section comprising a head, said first middle section comprising a thread configured to fit in said threaded bore, said second middle section comprising a section of reduced thickness having a length, and said bottom section comprising an end having a thickness greater than that of said section of reduced thickness; and
   c) a removable attachment comprising a second surface portion having a thickness, said second surface portion comprising a slit having a width, said slit surrounding said section of reduced thickness of said screw.

2. The assembly of claim 1, wherein said width of said slit is smaller than said thickness of said end of said screw.

3. The assembly of claim 1, wherein said slit comprises an open end and a closed end.

4. The assembly of claim 3, wherein said closed end of said slit is capable of gripping said end of said screw.

5. The assembly of claim 4, wherein said end of said screw has a cone surface directed towards said slit.

6. The assembly of claim 1, wherein said length of said section of reduced thickness is at least as great as said thickness of said second surface portion.

7. The assembly of claim 1, wherein said screw head comprises a structure configured for receiving a screwdriver.

8. An assembly comprising a joint endoprosthesis, a removable attachment part and a screw locking said attachment part and said joint endoprosthesis together, said screw being arranged in an area of overlapping first and second surface portions of said joint endoprosthesis and said attachment part, said first surface portion comprising a threaded bore receiving said screw, said screw comprising a shank of reduced thickness, and a thickened end adjacent to said shank, said shank lying in the area of said second surface portion, said second surface portion comprising a slit receiving said shank, said slit having a width smaller than the thickness of said thickened end.

9. The assembly of claim 8, wherein said slit comprises an open end and a closed end.

10. The assembly of claim 9, wherein said closed end of said slit at least partially receives said thickened end of said screw.

11. The assembly of claim 10, wherein said thickened end of said screw comprises a cone surface directed towards said slit.

12. A method of attaching an attachment part to a joint endoprosthesis, comprising:
   a) providing i) a joint endoprosthesis comprising a first surface portion, said first surface portion comprising a threaded bore configured for receiving a screw and a top surface, ii) a screw positioned in said first surface portion, said screw comprising a top section, adjacent first and second middle sections, and a bottom section, said top section comprising a head lying on said top surface of said first surface portion, said first middle section comprising a thread configured to fit in said threaded bore, said second middle section comprising a section of reduced thickness having a length, and said bottom section comprising an end having a thickness greater than that of said section of reduced thickness, and iii) a removable attachment comprising a second surface portion having a thickness, said second surface portion comprising a slit having a width;
   b) positioning said slit such that it surrounds said section of reduced thickness of said screw; and
   c) turning said screw such that said screw head moves off said top surface of said first surface portion.

13. The method of claim 12, wherein said width of said slit is smaller than said thickness of said end of said screw.

14. The method of claim 12, wherein said slit comprises an open end and a closed end.

15. The method of claim 14, wherein said closed end of said slit at least partially receives said end of said screw.

16. The method of claim 15, wherein said end of said screw has a cone surface directed towards said slit.

17. The method of claim 12, wherein said length of said section of reduced thickness is at least as great as said thickness of said second surface portion.

18. The method of claim 12, wherein said screw head comprises a structure configured for receiving a screwdriver.

* * * * *